United States Patent [19]
Amey

[11] Patent Number: 5,708,176
[45] Date of Patent: Jan. 13, 1998

[54] PREPARATION OF 3,5-LUTIDENE

[75] Inventor: Ronald Lee Amey, Wilmington, Del.

[73] Assignee: E. I. du Pont de Nemours and Company, Wilmington, Del.

[21] Appl. No.: 725,434

[22] Filed: Oct. 3, 1996

[51] Int. Cl.$^6$ .................. C07D 213/09; C07D 213/06
[52] U.S. Cl. .................................. 546/251; 546/250
[58] Field of Search ........................... 546/250, 251, 546/252

[56] References Cited

U.S. PATENT DOCUMENTS 5,149,816  9/1992  Goe et al. .................. 546/251

Primary Examiner—Alan L. Rotman

[57] ABSTRACT

The present invention is a process for the manufacture of 3,5-lutidine and 3-picoline from 2-methyl-1,5-pentanediamine by vapor phase reaction with hydrogen at about 400°–500° C. over an oxide catalyst.

5 Claims, No Drawings

PREPARATION OF 3,5-LUTIDENE

FIELD OF THE INVENTION

The present invention is a process for the manufacture of 3,5-lutidine and 3-picoline.

BACKGROUND OF THE INVENTION 3,5-Lutidine, also known as 3,5-dimethylpyridine, is used as a catalyst in epoxy cross-linking reactions, as a solvent in high temperature applications, and as an intermediate in the synthesis of pharmaceuticals, agrochemical, and corrosion inhibitors.

3-Picoline, also known as 3-methylpyridine, is used as an intermediate in the manufacture of niacin and niacinamide. It is also used as a solvent.

Reiff et al. (U.S. Pat. No. 3,803,152) teaches a method for producing pyridine or pyrrole from the gas phase reaction of glutaric or succinic acid dinitrile and hydrogen over a precious metal hydrogenation catalyst.

Verheijen and Duys (U.S. Pat. No. 4,189,585) teach a process for the preparation of pyridine and 2,6-lutidine from the demethylation of 2-picoline over a metallic hydrogenation catalyst at 250°–360° C.

Numerous patents teach technology relating to production of pyridine and alkyl-substituted pyridines from the reaction of carbonyl compounds and ammonia. For example, see U.S. Pat. Nos. 5,013,843, 4,481,361, 4,429,131 and 4,220,783.

Braden and Dieterich (U.S. Pat. No. 3,689,496) teach the production of alkyl pyridines from the reaction of a trimethanolalkane, R—C(CH$_2$OH)$_3$, with ammonia or an amine.

SUMMARY OF THE INVENTION

The present invention is a process for the synthesis of 3,5-lutidine from 2-methyl-1,5-pentanediamine by vapor phase reaction with hydrogen at about 400°–500° C. over an oxide catalyst. 3-Picoline is also produced by the reaction of the present process. These resultant products may be condensed and separated by distillation or other suitable means.

It is preferred to run the present process as a continuous process producing a product stream comprising the steps: (a) feeding hydrogen or hydrogen mixed with inert gases and volatilized 2-methyl-1,5-pentanediamine over an oxide catalyst at about 400°–500° C., (b) condensing liquid products from the product stream, and (c) recovering 3,5-lutidine and 3-picoline.

It is preferred that distillation is used to separate and recover the 3,5-lutidine and the 3-picoline products.

DETAILED DESCRIPTION OF THE INVENTION

The present invention concerns a process for the synthesis of 3,5-lutidine from a vapor phase reaction of 2-methyl-1,5-pentanediamine and hydrogen over an oxide catalyst at about 400°–500° C.

Along with 3,5-lutidine, 3-picoline is also produced. These resulting products may be condensed and separated by distillation or other suitable means. Yields of from the present process 3,5-lutidine are 10–25% by weight of the effluent product stream with remainder typically being 3-picoline and/or unreacted 2-methyl-1,5-pentanediamine.

It is preferred to practice the present process as a continuous process although the process could be as either a batch or continuous process. Heat needs to be provided to the reaction and may be supplied by any suitable means that achieves the reaction temperatures. Suitable reaction temperatures range from 350° to 550° C. A temperature range of 400° to 500° C. is preferred.

Suitable oxide catalysts include Al$_2$O$_3$, SiO$_2$, gamma-Al$_2$O$_3$, gamma-Al$_2$O$_3$/SiO$_2$, TiO$_2$, ZrO$_2$ or mixtures thereof. Al$_2$O$_3$ or Al$_2$O$_3$/SiO$_2$ are preferred. Gamma-Al$_2$O$_3$ or gamma-Al$_2$O$_3$/SiO$_2$ are most preferred. The weight ratio of Al$_2$O$_3$ to SiO$_2$ in the various mixed oxides may be varied from 9/1 to 1/9 in the oxide catalyst without substantial effect on the present process.

In a continuous process, the present process may be run as a fixed bed or fluid bed process. The particle size, shape or the nature of the particles of oxide catalyst are chosen to be suitable for the fixed or fluid bed process. Generally small attrition-resistant powders and/or particles are needed for fluid bed operation. A fixed bed process typically use pellets, spheres, or extrudates generally sized in the range of 1/16 to 1/4 inch diameter.

Hydrogen or hydrogen mixed with inert gasses, or mixtures thereof may be co-fed with vaporized organic feed. Inert gasses include those gases which do not react with the reactant or at the temperature conditions of the present process, for example nitrogen, helium or argon. The inert gas is used to provide dilution. A minimum of 4 moles of hydrogen for each one mole of 2-methyl-1,5-pentanediamine is needed for the process of the present invention. The ratio of the total moles gas feed (moles of hydrogen plus the moles of the inert dilution gas) to the moles of 2-methyl-1,5-pentanediamine for the present process may be from 5/1 to 40/1. A mole ratio from 20/1 to 30/1 is preferred. Reaction pressure for the present process may be from slightly above atmospheric to slightly below atmospheric pressure with atmospheric pressure preferred.

EXAMPLES

General

The reactor used in the Examples was a U-shaped glass reactor having one leg of a larger diameter that contained glass beads and functioned as a vaporizer section. The smaller diameter second leg contained the bed of catalyst. The reactor legs were approximately 490 mm long; the larger leg inside diameter was 19 mm; the smaller leg inside diameter was 10 mm.

The entire reactor unit was placed into an electrically heated sand bath with the temperature controlled by thermocouples and electronic temperature controllers. Both liquid and gas feeds were added to the top of the vaporizer section (downflow) and then passed through the catalyst bed (upflow) before being condensed, collected, and analyzed.

Gas flows are reported in standard cubic centimeters per unit time and were controlled by Brooks gas flowmeters. Liquid flows were controlled and metered by ISCO metering pumps.

Analyses of the product stream were accomplished by gas chromatography using 30 meter dB 1701 megabore column. The temperature program for the analysis was as follows: 90° C. with an increase in temperature of 6 deg/min to 200° C.; the temperature was held at 200° C. for 10 min. The injector temperature was 200° C.; the detector temperature was 250° C. Product streams were analyzed for 3,5-lutidine (LUT), unreacted 2-methyl-1,5-pentanediamine (MPMD), 3-picoline (3PIC), and, where appropriate, trace impurities (mass spectroscopy was used to identify unknowns). Values reported in the Tables below are in area percent.

Example 1

This example illustrates the use of a gamma-$Al_2O_3$ catalyst. 6.11 g of 99% gamma-$Al_2O_3$ in the form of ⅛ inch tables (Johnson Matthey catalyst, Catalog #1286, Lot No. D17A03) was activated by treatment for 1 hr at 400° C. with a flow of 80 cc/min of hydrogen. A hydrogen flow of 30 cc/min and a MPMD flow of 0.3 cc/hr were used during the reaction. The temperature was raised from 400° to 450° C. after 2 hours of operation and to 500° C. after 5 hours of operation. The results are presented in TABLE 1.

TABLE 1

| Time, hr | Temperature, °C. | LUT, % | 3PIC, % |
| --- | --- | --- | --- |
| 1.0 | 400 | 16.4 | 69.9 |
| 2.0 | 400 | 18.7 | 55.8 |
| 3.0 | 450 | 12.7 | 61.9 |
| 4.0 | 450 | 15.8 | 67.4 |
| 5.0 | 450 | 15.3 | 66.0 |
| 6.0 | 500 | 13.5 | 70.6 |
| 7.0 | 500 | 13.1 | 70.7 |

Example 2

This example illustrates a second form of an oxide catalyst. 6.01 g of gamma-$Al_2O_3$ in the form of ⅛ inch extrudate (Engelhard Al-4198, Lot No. 583A-22-33-41) was placed in the reactor tube and activated by treatment for 1 hour at 400° C. with 80 cc/min of hydrogen.

The reactant streams were passed over the catalyst at a hydrogen flow of 30 cc/min and a MPMD flow of 0.3 cc/hr. The temperature of the reactor was raised from 400° C. to 450° C. after 4 hours of operation and maintained for an additional 14 hours.

The weight percent of the reaction products, 3,5-lutidine (LUT) and 3-picoline (3PIC) is shown in Table 2 as a function of the reaction temperature.

TABLE 2

| Time, hr | Temperature, °C. | LUT, % | 3PIC, % |
| --- | --- | --- | --- |
| 1.0 | 400 | 18.6 | 25.1 |
| 2.0 | 400 | 15.5 | 22.1 |
| 4.0 | 400 | 12.2 | 24.1 |
| 5.5 | 450 | 21.6 | 37.6 |
| 6.0 | 450 | 23.6 | 43.8 |
| 8.0 | 450 | 23.5 | 50.8 |
| 10.0 | 450 | 23.5 | 44.5 |
| 12.0 | 450 | 22.1 | 48.2 |
| 14.0 | 450 | 20.0 | 50.8 |
| 16.0 | 450 | 21.8 | 50.1 |
| 18.0 | 450 | 22.0 | 47.4 |

I claim:

1. A process for the preparation of 3,5-lutidine and 3-picoline which comprises reacting in vapor phase 2-methyl-1,5-pentanediamine and hydrogen or hydrogen mixed with an inert gas over an oxide catalyst at temperatures from about 400° to 500° C. wherein the hydrogen or hydrogen mixed with the inert gas is present in a molar ratio from about 5/1 to 40/1 compared to the molar concentration of 2-methyl-1,5-pentanediamine and the oxide catalyst is selected from the group consisting of gamma-$Al_2O_3$, gamma-$Al_2O_3$/$SiO_2$, $ZrO_2$ or mixtures thereof.

2. The process according to claim 1 wherein the process is continuous and produces a product stream comprising the steps: (a) feeding hydrogen or hydrogen mixed with inert gases and volatilized 2-methyl-1,5-pentanediamine over an oxide catalyst at about 400°–500° C., (b) condensing liquid products from the product stream, and (c) recovering 3,5-lutidine and 3-picoline.

3. The process of claim 2 where distillation is used to separate and recover 3,5-lutidine and 3-picoline.

4. The process of claim 3 where the oxide catalyst is chosen from the group consisting of gamma-$Al_2O_3$, gamma-$Al_2O_3$/$SiO_2$, $ZrO_2$ or mixtures thereof.

5. The process of claim 3 where the oxide catalyst is gamma-$Al_2O_3$ or gamma-$Al_2O_3$/$SiO_2$.

* * * * *

UNITED STATES PATENT AND TRADEMARK OFFICE
CERTIFICATE OF CORRECTION

PATENT NO.  : 5,708,176
DATED       : January 13, 1998
INVENTOR(S) : Ronald Lee Amey It is certified that error appears in the above-indentified patent and that said Letters Patent is hereby corrected as shown below:

On the title page, item [54] and column 1, line 1,
    The title should read "Preparation of 3,5-Lutidine"

instead of "Preparation of 3,5-Lutidene".

Signed and Sealed this

Thirty-first Day of March, 1998

Attest:

BRUCE LEHMAN

Attesting Officer        Commissioner of Patents and Trademarks